United States Patent [19]

Reuter et al.

[11] Patent Number: 4,835,187

[45] Date of Patent: * May 30, 1989

[54] SPRAY DRIED IBUPROFEN

[75] Inventors: Gerald L. Reuter, Plattsburgh, N.Y.; Maureen M. Harrison, St. Albans, Vt.

[73] Assignee: American Home Products Corporation, New York, N.Y.

[*] Notice: The portion of the term of this patent subsequent to May 30, 2006 has been disclaimed.

[21] Appl. No.: 62,732

[22] Filed: Jun. 15, 1987

[51] Int. Cl.$^4$ .............................................. A61K 31/74
[52] U.S. Cl. .................................... 514/570; 424/489; 514/974
[58] Field of Search ....................... 514/557, 974, 570; 424/484, 486, 488, 485, 456, 489, 78

[56] References Cited

U.S. PATENT DOCUMENTS

| | | | |
|---|---|---|---|
| 4,569,937 | 2/1986 | Baker et al. | 514/282 |
| 4,571,400 | 2/1986 | Arnold | 514/557 X |
| 4,681,897 | 7/1987 | Brand | 514/557 |
| 4,684,666 | 8/1987 | Haas | 514/557 |
| 4,689,218 | 8/1987 | Gazzaniga et al. | 514/557 X |
| 4,690,823 | 9/1987 | Tonner et al. | 424/456 |
| 4,695,591 | 9/1987 | Honna | 514/781 |
| 4,713,249 | 12/1987 | Schröder | 424/488 |
| 4,726,966 | 2/1988 | Kowoshima et al. | 514/974 |

FOREIGN PATENT DOCUMENTS 0190826  8/1986  European Pat. Off. ............ 514/974

Primary Examiner—Joseph L. Schofer
Assistant Examiner—Peter F. Kulkosky
Attorney, Agent, or Firm—John W. Routh

[57] ABSTRACT

A therapeutic taste-neutral powder form a ibuprofen obtained by spray-drying a suspension of colloidal silica in a lower alkanol solution of ibuprofen and a cellulose material such as ethyl cellulose, hydroxyethyl cellulose and hydroxypropylmethyl cellulose.

9 Claims, No Drawings

SPRAY DRIED IBUPROFEN

BACKGROUND OF THE INVENTION (a) Field of the Invention

This invention relates to a novel therapeutic form of spray dried ibuprofen having a neutral taste which can be formulated into, for example, chewable tablets and fast dissolving dosage forms as described in U.S. Pat. Nos. 4,305,502 and 4,371,516. More specifically this invention relates to a taste-neutral spray dried powder formed by spray drying a solution of ibuprofen and ethylcellulose, hydroxyethyl cellulose or hydroxypropylmethyl cellulose alone or in admixture, in at least a 50% lower alkanol solution having suspended therein colloidal silica. By taste-neutral it is meant that the powder has essentially no taste and is neither sweet nor bitter.

(b) Prior Art

Ibuprofen, a widely used analgesic and antipyretic, is not palatable enough to be used in chew-type tablets for those people who do not swallow whole solid-type dosage forms.

The use of flavor agents eg. chocolate, banana, orange, lemon, licorice, root beer, and raspberry, in particular, have been proposed for bitter tasting drugs. These agents are not dependable masking ingredients. Mint flavors can be useful in ameliorating a chalky taste parameter. Bitter properties, however, are very difficult to mask to any great extent, particularly, when they do not mimic the expected natural taste of the flavor agent.

Other properties including mouthfeel also need to be addressed in consideration of the oral acceptance of chewable or chew-type tablets.

The fast dissolving dosages forms described in U.S. Pat. Nos. 4,305,502 and 4,371,516 are manufactured to disintegrate in water within five seconds or less and hence dissolve rapidly in the saliva of the mouth. Heretofore the use of such dosage forms are restricted to pharmaceuticals which had a neutral taste or a slightly disagreeable taste which could be masked by a flavoring agent. Pharmaceuticals with a bitter taste such as ibuprofen are not currently used in such dosage forms.

SUMMARY OF THE INVENTION

According to this invention, a novel therapeutic taste-neutral powder form of spray-dried ibuprofen is provided which can be formulated into chewable tablets and the like. The powder is formed by spray drying a solution of ibuprofen and ethyl celluose, hydroxyethyl cellulose or hydroxypropylmethyl cellulose, alone or in admixture, in at least a 50% lower alkanol solution having colloidal silica suspended therein. Preferably the lower alkanol is isopropanol.

According to another aspect of this invention, a pharmaceutical dosage form for oral administration as a solid is provided, which dosage form can be disintegrated by water at 37° C. within ten seconds, and comprises as the pharmaceutical agent incorporated therein the taste neutral powder form of spray dried ibuprofen of this invention.

DETAILS OF THE INVENTION

The ibuprofen useful in this invention is the pharmaceutical grade. The ethyl cellulose and hydroxyethyl cellulose useful in this invention are the National Formulary or pharmaceutical grade. Suitable grades are the medium type and standard grades marketed by Dow Chemical Company, Midland, Mich. under the Ethocel trademark. Other suitable grades are those marketed by Hercules, Inc. of Wilmington, Del. and Biddle-Sawyer Corp. of New York, N.Y. Ethocel is an organo soluble ethyl ether of cellulose containing between 2.25 and 2.58 ethoxy groups per glucose unit corresponding to an ethoxy range of 45 to 49.5%.

Suitable grades of hydroxyethyl cellulose are marketed by Hercules, Inc. of Wilmington, Del. under the National trademark. Hydroxyethyl cellulose is the hydroxyethyl ether of cellulose. The Natrosol grades are 150, 180, 250 and 300 containing between 1.5 and 3.0 ethoxy groups per glucose unit. Food grades are Natrosol 250 L, 250 H and 250 HH having molecular weights respectively of 75,000; 900,000 and 1,200,00 ranging from low viscosity to high viscosity materials. Mixtures of grades can be used.

Suitable grades of hydroxypropyl methylcellulose for use in the present invention are the Methocel brand, made by Dow Chemical Company, Midland, Mich., U.S.A., grades E, F and K having a viscosity range of about 3500 to about 5600 cps and preferably a viscosity of about 4000 cps.

Also suitable grades of hydroxypropyl methylcellulose are the Metolose brand, made by Shin-Etsu Chemical Co., Ltd., grades 60 SH, 65 SH and 90 SH having a viscosity range of about 3500 to about 5600 cps and preferably a viscosity of about 4000 cps.

Methocel F is a grade of hydroxypropyl methylcellulose containing about 27 to 30% methoxyl content and from about 4.0 to 7.5% hydroxypropoxyl content calculated on the dried basis. Methocel K is a grade of hydroxypropyl methylcellulose containing about 19 to 25% methoxyl content and from about 4 to 12% hydroxypropoxyl content calculated on the dried basis.

The preferred grade of hydroxypropyl methylcellulose for use in the present invention is hydroxypropyl methylcellulose USP, 2910, 4000 cps (Methocel E4MP) which is a propylene glycol ether of methylcellulose containing not less than 28.0% and not more than 30.0% methocyl content, and not less than 7.0% and not more than 12.0% hydroxypropoxyl content.

The colloidal silica useful in this invention has a particle size of about 10 millimicrons. Suitable grades are Cabosil-M-5 marketed by Cabot Corporation of Boston, Mass., and that sold by PQ Company, Philadelphia, Pa.

The weight percent of ibuprofen in the taste neutral powder can be from about 40 to 70% by weight and the weight percent of the cellulose can range from 15% to 50% by weight. At 155 by weight of cellulose, there may be a slightly bitter taste but at 20% and above the powder is taste neutral. The weight percent of colloidal silica in the taste neutral powder can be from about 5% to 40% by weight.

The solvent for the cellulose can be one of the alkanols such as methyl, ethyl, isopropyl or mixtures thereof, or at least 50% solutions thereof, but must be an solvent in which the ibuprofen is soluble and the celluloses are soluble or dispersible. By alcohol solutions is meant aqueous solutions.

A small amount of a hydrophobic substance such as castor oil can be added to the solution to inhibit leaching of the ibuprofen from the spray dried powder. A small amount of glyceryl monostearate can be added to improve taste masking. Plasticisers can include, in addition to castor oil, diethyl phthalate, triacetin and tributyl citrate.

Food acids, eg. fumaric acid and malic acid, which are soluble in alkanol solutions and can create an aqueous environment not greater than pH 4.0, may correct the perception of bitterness in preparing the spray dried powder.

Spray dryers can be of the usual laboratory or commercial type. Suitable spray dryers are manufactured by Buchi Laboratoriums-Technik AG, by the Anhydro Company of Attleboro, Mass. and Niro Atomizer Inc., of Columbia, Md.

The spray dryer employed in the following examples was a Buchi 190 Mini Spray Dryer. The operating conditions for the Buchi Mini Spray Dryer are customarily an inlet temperature of 153° to 210° C. and a corresponding outlet temperature range of 94° to 108° C.

The following examples illustrate the formation of the taste-neutral spray dried ibuprofen powder of the invention. In these examples, the hydroxy ethyl cellulose was obtained from Hercules Chemical Company, Wilmington, Del. It was a dry material of the standard low viscosity type having a molecular weight of about 75,000.

EXAMPLE 1

In this example, the feed mixture to the spray dryer was composed of the following materials.

| Ingredient | Weight % Solids in powder | Grams Ingredient in suspension |
|---|---|---|
| Ibuprofen, USP | 60.6 | 100 |
| Hydroxyethyl Cellulose, NF | 30.3 | 50 |
| Colloidal Silica | 6.06 | 10 |
| Castor Oil | 3.03 | 5 |
| Isopropyl Alcohol, 67% | — | q.s 1000 ml. |
| Total: | 100% | 1165 grams |

The ibuprofen was dissolved in a portion of the alcohol contained in a stainless steel mixing vessel with the aid of a Lightnin mixer. The hydroxyethyl cellulose was wetted and dispersed in the remaining alcohol in a separate stainless steel mixing vessel with the aid of a Lightnin mixer. The contents of the two mixing vessels were filtered and combined. The caster oil and then colloidal silica were added and mixed until a homogeneous dispersion was obtained. The dispersion was then transferred to the feed hopper of the Buchi Mini Spray Dryer.

The spray dryer was operated such that an air inlet temperature of 153°–210° C. and an air outlet temperature of 94° to 108° C. was maintained throughout the run.

The yield of spray dried powder was about 90% of theoretical. The product was a white, fine powder.

The freshly obtained product upon tasting and beng held in the mouth for 45 seconds produced no bitterness characteristic of ibuprofen. Upon aging one month at room temperature the product remained quite acceptable without bitterness.

EXAMPLE 2

This example describes the preparation of fast dissolving dosage forms using the spray dried taste-neutral ibuprofen of Example 1 and other ingredients as follows:

| Ingredient | Weight % suspension | Grams in suspension |
|---|---|---|
| Gelatin, BY 19/50 | 4.0 | 10.00 |
| Mannitol, granular | 3.0 | 7.50 |
| Deionized water | 67.10 | 167.75 |
| NUTRASWEET, NF | 1.20 | 3.00 |
| Cherry #271 | 0.40 | 1.00 |
| Cream Flavor #59.200/A | 0.20 | 0.50 |
| Sodium lauryl sulfate | 0.10 | 0.25 |
| Croscarmellose sodium, Type A | 1.00 | 2.50 |
| Powder, Example 1 | 23.0 | 57.50 |

The procedure for preparing a batch of the above suspension takes place in two stages, i.e. the preparation of the gelatin base and the addition of the pharmaceutical agent.

The gelatin base is prepared by adding the gelatin to the deionized water at 30° C. and mixing until the gelatin is dissolved. The solution is then cooled to 25° C. and the mannitol, the sodium lauryl sulfate, the sweetner, and the flavors are separately added and dissolved.

The croscarmellose sodium in powder form (Ac-DiSol) and the taste-neutral spray dried ibuprofen powder was dry mixed and screened through a 20 mesh screen. The mixed powder is added to the gelatin solution and further admixed with a homomixer for thirty minutes to form a uniform dispersion.

The freeze dryer employed in this example is a Virtis 25 SRC Model Freeze Dryer. The fast dissolving dosage forms are prepared by dosing 500 milligrams of the suspension of ibuprofen into each well in a thermoformed blister tray containing 10 wells per tray. The filled trays are placed in a larger tray containing a dry ice-methanol mixture. When the suspension in the wells are frozen, the samples are placed on the freeze dryer trays at a shelf temperature of −45° C.

When the samples have reached a temperature of −45° C., as determined by a probe in a well, the condenser is turned on and the freezer turned off. The condenser temperature is brought to between −40° and −45° C. and the vacuum is turned on to between 50 and 60 millitorrs. The heater is then turned on and the shelf temperature is adjusted to 50°–55° C. The heat-dry cycle lasts for 4 hours. The vacuum, the condenser and the heater are turned off and the samples removed. The wafers from each batch are removed from the wells in the trays. They are white in color and each weights about 150 milligrams of which about 80 milligrams is ibuprofen. The wafers from each batch when placed on the tongue exhibit a cherry/cream flavor with a very slight bitter after taste. When placed in water at 37° C. the wafers disintegrate in less than ten seconds.

EXAMPLE 3

This example describes the preparation of a chewable tablet using the spray dried taste neutral ibuprofen of Example 2 and other ingredients as follows:

| Ingredients | Weight |
|---|---|
| Powder of Example 1, | 1320 mg |
| Cornstarch | 200 mg |
| Mannitol | 740 mg |
| Sorbital | 740 mg |
| Total | 3000 mg |

The powder of Example 1 contained 60.6% by weight or 800 mg of ibuprofen. The ingredients were mixed in a suitable mixer and formed into tablets using a 29 mm punch and die set on a Carver Press. Compression was accomplished at 5000 psi. The tablets when chewed in the mouth had a neutral taste and good mouthfeel. The taste could be improved by incorporation into the tablet of suitable flavoring agents such as a mint flavoring agent.

EXAMPLE 4

In this example, the feed mixture to the spray dryer was composed of the following materials.

| Ingredient | Weight % Solids in powder | Grams Ingredient per 100 ml of suspension |
|---|---|---|
| Ibuprofen, USP | 53.2 | 125 |
| Isopropyl Alcohol | — | 200.00 |
| Ethyl Cellulose, NF | 21.3 | 50 |
| Colloidal Silica | 17% | 40 |
| Castor Oil | 4.25 | 10 |
| Fumaric Acid | 4.25 | 10 |
| Isopropyl Alcohol | — | q.s. 1000 ml. |
| Total: | 100% | |

The ibuprofen was dissolved in a portion of the alcohol contained in a stainless steel mixing vessel with the aid of a Lightnin mixer. All was dissolved in 3 hours except for a small residue. The ethyl cellulose was dissolved in a second portion of the alcohol in a separate stainless steel mixing vessel. The ethylcellulose did not dissolve in 2 hours but was left overnight and by morning it was mostly dissolved. After one hour mixing with the Lightnin mixer, it was completely solubilized. The contents of the two mixing vessels were then combined. The castor oil, then the colloidal silica and then the fumaric acid were added and mixed until a homogeneous dispersion was obtained. Isopropyl alcohol was then added q.s. to 1000 ml. The dispersion was then transferred to the feed tank of the Buchi Mini Spray Dryer.

The spray drier was operated such that an air inlet temperature of 153°–210° C. and an air outlet temperature of 94°–108° C. was maintained throughout the run.

The freshly obtained white powder upon tasting was taste neutral.

EXAMPLE 5

In this example, ethyl alcohol was used instead of isopropyl alcohol and the feed mixture to the spray dryer was composed of the following materials.

| Ingredient | Grams Ingredient per 1000 ml suspension | Weight % Solids in Powder |
|---|---|---|
| Ibuprofen, USP | 115 | 54.8 |
| Ethyl Cellulose, NF | 50 | 23.8 |
| Colloidal Silica | 25 | 11.9 |
| Hydroxypropylmethyl Cellulose | 5 | 2.4 |
| Castor Oil | 10 | 4.8 |
| Fumaric Acid | 5 | 2.4 |
| Ethyl Alcohol | q.s. 1000 ml. | 100% |

Ethyl alcohol in the amount of 200 ml was placed in a stainless steel mixing vessel equipped with a Lightnin mixer and 115 grams of ibuprofen were added. After mixing for one hour, the ibuprofen had dissolved. Ethyl alcohol in the amount of 600 ml was placed in another stainless steel mixing vessel equipped with a Lightnin mixer and the speed was adjusted to produce a vortex. The ethyl cellulose (50 grams) and the hydroxypropylmethyl cellulose were then added and mixing continued for one hour until the ethyl cellulose had dissolved. The contents of the two mixing vessels were combined and ethyl alcohol added q.s. to 1000 ml. Mixing was continued for one half hour until all solids had dissolved.

The thousand milliliters of this solution were then transferred to a separate mixing vessel and the ten grams of castor oil and then the 25 grams of colloidal silica were added with mixing until uniform. In order to improve dispersion of the colloidal silica, five grams of fumaric acid were added. The dispersion was then transferred to the feed tank of the Buchi Portable Spray Dryer.

The spray dryer was operated such that an air inlet temperature of 120°–122° C. and an air outlet temperature of 78°–82° C. was maintained through the run.

Additional formulations were prepared essentially using the procedure of Example 5 wherein the ibuprofen and the cellulose materials were dissolved in separate portions of alcohol, the combined solutions were filtered and the colloidal silica and other ingredients added and stirred until a homogeneous solution was obatined. The mixture was stirred to maintain homogenity and spray dried at controlled temperatures and liquid feed rate to obtain a dry powder. The ingredients in these additional formulations are shown in the following Table I.

TABLE I

| Ingredient | Example 6 Grams | Example 6 %* | Example 7 Grams | Example 7 %* | Example 8 Grams | Example 8 %* |
|---|---|---|---|---|---|---|
| Ibuprofen | 100 | 55.6 | 85 | 50.0 | 60 | 42.9 |
| Colloidal Silica | 25 | 13.9 | 30 | 17.6 | 25 | 17.9 |
| Hydroxyethyl Cellulose | 50 | 27.8 | 20 | 11.8 | — | — |
| Hydroxypropyl-methyl Cellulose | — | — | 30 | 17.6 | 50 | 35.7 |
| Castor Oil | 5 | 2.7 | 5 | 2.9 | 5 | 3.5 |
| Ethyl Alcohol, q.s. ad. | | | 1000 | | | |
| Isopropyl Alcohol, 65 q.s. ad. | 1000 | | 1000 | | | |

*Weight percent ingredient in spray dried powder

We claim:

1. A therapeutic taste neutral powder form of spray-dried ibuprofen which consists essentially of, based upon the weight of the powder, about 40% to 70% by weight ibuprofen, about 15% to 50% by weight of a cellulose material selected from the class consisting of ethylcellulose, hydroxyethyl cellulose, hydroxypropylmethyl cellulose and admixtures thereof and about 5% to 40% by weight colloidal silica, the powder having been spray dried from a suspension of the colloidal silica in a lower alkanol solution of the ibuprofen and the cellulose material, the lower alkanol containing up to 50% water.

2. In a pharmaceutical dosage form for oral administration as a solid, which dosage form can be distinguished by water within ten seconds, the improvement which comprises incorporating into such dosage form as the pharmaceutical substance a therapeutic taste-neutral powder form of spray-dried ibuprofen which consists essentially of, based upon the weight of the powder, about 40% to 70% by weight ibuprofen, about 15% to 50% by weight of a cellulose material selected from the class consisting of ethylcellulose, hydroxyethyl cellulose, hydroxypropylmethyl cellulose and admixtures thereof and about 5% to 40% by weight colloidal silica, the powder having been spray dried from a suspension of the colloidal silica in a lower alkanol solution of the ibuprofen and the cellulose material, the lower alkanol containing up to 50% water.

3. The taste neutral powder of claim 1 wherein the lower alkanol is isopropyl alcohol.

4. The taste neutral powder of claim 2 wherein the lower alkanol is isopropyl alcohol.

5. In a pharmaceutical dosage form for oral administration as a solid chewable taste-neutral tablet containing ibuprofen, the improvement which comprises incorporating into such tablet as the pharmaceutical substance a therapeutic taste-neutral powder form of spray-dried ibuprofen which consists essentially of, based upon the weight of the powder, about 40% to 70% ibuprofen, about 15% to 50% by weight of a cellulose material selected from the class consisting of ethylcellulose, hydroxyethyl cellulose, hydroxypropylmethyl cellulose and admixtures thereof, and about 5% to 40% by weight colloidal silica, the powder having been spray dried from a suspension of the colloidal silica in a lower alkanol solution of the ibuprofen and the cellulose material, the lower alkanol containing up to 50% water.

6. The dosage form of claim 3 wherein the lower alkanol is isopropyl alcohol.

7. The taste neutral powder of claim 1 wherein the cellulose is hydroxyethyl cellulose.

8. The dosage form of claim 2 wherein the cellulose is hydroxyethyl cellulose.

9. The dosage form of claim 3 wherein the cellulose is hydroxyethyl cellulose.

* * * * *